United States Patent [19]

Kis et al.

[11] Patent Number: 5,573,773
[45] Date of Patent: Nov. 12, 1996

[54] STABLE HIGHLY CONCENTRATED FORMULATIONS OF FLUORESCEIN DERIVATIVES

[75] Inventors: Gyoergy L. Kis, Triboltingen; Ernst D. Wachsmuth, Binningen, both of Switzerland

[73] Assignee: Ciba Geigy Corporation, Tarrytown, N.Y.

[21] Appl. No.: 392,993

[22] PCT Filed: Sep. 2, 1993

[86] PCT No.: PCT/EP93/02367

§ 371 Date: Mar. 6, 1995

§ 102(e) Date: Mar. 6, 1995

[87] PCT Pub. No.: WO94/05331

PCT Pub. Date: Mar. 17, 1994

[30] Foreign Application Priority Data

Sep. 10, 1992 [DE] Germany ................ 928 10 695.4

[51] Int. Cl.$^6$ .................. A61F 2/02; A61K 31/715; A61K 47/40; C07H 15/04
[52] U.S. Cl. .................. 424/423; 424/427; 424/428; 514/58; 514/777; 514/912; 536/120
[58] Field of Search .................. 424/423, 427, 424/428; 514/777, 912, 58; 536/120

[56] References Cited

U.S. PATENT DOCUMENTS 5,227,372  7/1993  Folkman ................... 514/912

FOREIGN PATENT DOCUMENTS 149197     12/1984  European Pat. Off. .
279757      2/1988  European Pat. Off. .
447351A1    3/1991  European Pat. Off. .

OTHER PUBLICATIONS

Diabetic Cataract: Prevention by Photo affinity Drug, Sihn Van Chow, Chem. Abstracts, vol. 105, No. 19, 1984.

EP Search Report.

Primary Examiner—Carlos Azpuru
Attorney, Agent, or Firm—Edward McC. Roberts; R. Scott Meece; Michael U. Lee

[57] ABSTRACT

The present invention relates to stable highly concentrated formulations of specific fluorescein derivatives, to the preparation of said formulations and the use thereof, especially for the photodynamic therapy of secondary cataract.

The invention principally relates to an aqueous solution comprising a fluorescein diester, preferably a fluorescein di-lower alkyl ester, most preferably fluorescein diacetate, and a partially etherified β-cyclodextrin the ether substituents of which are hydroxyethyl, hydroxypropyl or dihydroxypropyl groups, some of which ether substituents may be methyl or ethyl groups, said β-cyclodextrin ether having a water-solubility of more than 1.8 g in 100 ml of water, preferably hydroxy-β-cyclodextrin.

21 Claims, No Drawings

STABLE HIGHLY CONCENTRATED FORMULATIONS OF FLUORESCEIN DERIVATIVES

The present invention relates to stable highly concentrated formulations, in particular solutions, of specific fluorescein derivatives, to the preparation of said formulations and the use thereof, especially for photodynamic therapy, preferably for the treatment or prevention of secondary cataract. The formulations of the present invention include a fluorescein diester and a partially etherified β-cyclodextrin, the ether substituents of which are hydroxyethyl, hydroxypropyl or dihydroxypropyl groups, some of which ether substituents may be methyl or ethyl groups.

The fluorescein derivatives are special diesters of fluorescein, preferably fluorescein diacetate. The novel formulations contain as component that makes possible the preparation of stable and highly concentrated solutions of these fluorescein derivatives special cyclodextrin derivatives, in particular hydroxypropyl-β-cyclodextrin.

Pharmaceutical compositions of sparingly water-soluble or unstable medicaments and the preparation thereof are taught in EP-A-149 197. This patent specification also postulates, inter alia, hydroxypropyl-β-cyclodextrin for use with drugs such as indomethacin or dexamethason.

It has already been proposed in EP-A-447 351 to complex fluorescein with a cyclodextrin sulfate and to make it available in this form as an ophthalmological agent.

In contradistinction to this prior art, formulations comprising fluorescein diacetate and a compound of the hydroxypropyl-β-cyclodextrin type have hitherto not been disclosed. Surprisingly, however, it has been found that such formulations afford unexpected advantages over the closest prior art, especially in view of the use of such formulations in the field of the photodynamic therapy of secondary cataract. The novel formulations have been found to be, inter alia, unexpectedly stable, and it is also possible with these formulations to dissolve fluorescein diacetate in the sufficiently high concentrations necessary for photodynamic therapy, typically for the treatment or prevention of secondary cataract, in order to make this therapy practicable.

The present invention therefore relates primarily to a formulation, conveniently an aqueous solution, comprising a fluorescein diester, preferably a fluorescein di-lower alkyl ester, and a partially etherified β-cyclodextrin the ether substituents of which are hydroxyethyl, hydroxypropyl or dihydroxypropyl groups, some of which ether substituents may be methyl or ethyl groups. Preferably the β-cyclodextrin ether has a water-solubility of more than 1.8 g in 100 ml of water. The present invention also relates to dry formulations comprising a fluorescein diester, preferably a fluorescein di-lower alkyl ester, and a partially etherified β-cyclodextrin the ether substituents of which are hydroxyethyl, hydroxypropyl or dihydroxypropyl groups, some of which ether substituents may be methyl or ethyl groups, from which the above described solutions can be reconstituted. The β-cyclodextrin ether preferably has a water-solubility of more than 1.8 g in 100 ml of water.

The term "lower" used in the context of this invention denotes radicals or groups containing up to 7, preferably up to 4, carbon atoms.

Lower alkyl is alkyl of up to 7, preferably of up to 4, carbon atoms, and is typically methyl, ethyl, propyl, 2-propyl, butyl, tert-butyl, pentyl or 2,2-dimethylpropyl.

The fluorescein diester is conveniently an ophthalmogically acceptable diester of fluorescein. Suitable diesters are typically fluorescein diphosphate or fluorescein di-lower alkyl esters such as fluorescein diacetate, fluorescein dibutyrate or fluorescein dipivalate. The fluorescein diester may also be a mixed diester, conveniently a fluorescein monophosphate-monoacetate, or a mixed fluorescein monoacetate-monobutyrate. Fluorescein diacetate is particularly preferred.

The novel solutions typically contain the fluorescein diester in a concentration of up to about 200 micromol/l (200 µmol/l), preferably in a concentration of about 40 to about 200 micromol/l, more particularly in a concentration of up to about 100 micromol/l and, most preferably, in a concentration of about 60 to about 100 micromol/l.

Partially etherified β-cyclodextrins the ether substituents of which are hydroxyethyl, hydroxypropyl or dihydroxypropyl groups, some of which ether substituents may be methyl or ethyl groups, said β-cyclodextrin ether having a water-solubility of more than 1.8 g in 100 ml of water, have already been disclosed in EP-A-149 197. The β-cyclodextrin derivatives used in the practice of this invention are advantageously ophthalmogically acceptable and, moreover, nontoxic. β-Cyclodextrin is a cyclic compound consisting of seven anhydroglucose units. It is also known as cycloheptaamylose. Each of the seven glucose rings contains three hydroxyl groups which may be etherfied. The hydroxy groups are in 2-, 3- and 6-position. In the partially etherified cyclodextrin derivatives which are used in the practice of this invention, only some of the hydroxy groups are etherified with the indicated hydroxyalkyl radicals as well as in some cases with methyl or ethyl groups. In the etherification with hydroxyalkyl radicals, which can be effected by reaction with the appropriate alkylene oxides, the degree of substitution is indicated as molar degree of substitution (MS) in mol of alkylene oxide per anhydroglucose unit. In the hydroxyalkyl ethers of β-cyclodextrin used in the practice of this invention, the molar degree of substitution is typically from 0.05 to 10, preferably from 0.2 to 2. A molar degree of substitution of about 0.25 to about 1 is especially preferred.

The partially etherified β-cyclodextrins which are used in the novel formulations may contain, in addition to the hydroxyalkyl radicals, also alkyl radicals, namely methyl or ethyl radicals, up to a degree of substitution of 0.05 to 2.0, preferably of 0.2 to 1.5. The degree of substitution for the alkyl radicals is most preferably about 0.5 to about 1.2.

Typical examples of the partially etherified β-cyclodextrin derivatives that are used in the novel formulations are hydroxyethyl-β-cyclodextrin, hydroxypropyl-β-cyclodextrin, dihydroxypropyl-β-cyclodextrin, mixed forms thereof. e.g. hydroxyethyl-hydroxypropyl-β-cyclodextrin, and also mixed ethers containing methyl or ethyl groups, typically methylhydroxyethyl-β-cyclodextrin, methylhydroxypropyl-β-cyclodextrin, ethylhydroxyethyl-β-cyclodextrin or ethylhydroxypropyl-β-cyclodextrin. Hydroxypropyl-β-cyclodextrin is especially preferred.

The solubility of the fluorescein diesters is increased in particular by their forming inclusion compounds with the etherified β-cyclodextrins. The novel formulations therefore contain the partially etherified β-cyclodextrins in an amount which ensures that the amount of fluorescein diester used is completely dissolved. The novel formulations will preferably contain the partially etherified β-cyclodextrins in an amount of about 1 to about 20 percent by weight, most preferably in an amount of about 5 to about 12 percent by weight.

A preferred embodiment of the present invention therefore relates to a solution comprising a fluorescein di-lower alkyl ester and a partially etherified β-cyclodextrin the ether substituents of which are hydroxyethyl, hydroxypropyl or dihydroxypropyl groups.

A particularly preferred embodiment of the present invention therefore relates to a solution comprising fluorescein diacetate, and a partially etherified β-cyclodextrin the ether substituents of which are hydroxyethyl, hydroxypropyl or dihydroxypropyl groups.

A further preferred embodiment of the present invention relates to a solution comprising fluorescein diacetate and a partially etherified β-cyclodextrin the ether substituents of which are hydroxypropyl groups.

In particular, the invention relates to a solution comprising about 40 to about 200 micromol/l of fluorescein diacetate and about 1 to about 20 percent by weight of hydroxypropyl-β-cyclodextrin. Most preferably, the invention relates to a solution comprising about 60 to about 100 micromol/l of fluorescein diacetate and about 5 to about 12 percent by weight of hydroxypropyl-β-cyclodextrin.

A preferred embodiment of this invention also relates to a dry formulation comprising a fluorescein di-lower alkyl ester and a partially etherified β-cyclodextrin the ether substituents of which are hydroxyethyl, hydroxypropyl or dihydroxypropyl groups.

A particularly preferred embodiment of the invention relates to a dry formulation comprising a fluorescein diacetate and a partially etherified β-cyclodextrin the ether substituents of which are hydroxyethyl, hydroxypropyl or dihydroxypropyl groups.

A further preferred embodiment of the invention relates to a dry formulation comprising a fluorescein di-lower alkyl ester and a partially etherified β-cyclodextrin the ether substituents of which are hydroxypropyl groups.

In particular, the invention relates to a dry formulation suitable for reconstituting a solution comprising about 40 to about 200 micromol/l of fluorescein diacetate and about 1 to about 20 percent by weight of hydroxypropyl-β-cyclodextrin. Most preferably, the invention relates to a dry formulation suitable for reconstituting a solution comprising about 60 to about 100 micromol/l of fluorescein diacetate and about 5 to about 12 percent by weight of hydroxypropyl-β-cyclodextrin.

In addition to the two cited components, the novel aqueous solution may also comprise further components, including isotonising agents, pH regulators, solvents, solubilisers, thickeners or buffers.

Suitable isotonising agents are preferably non-ionic isotonising agents such as urea, glycerol, sorbitol, mannitol, aminoethanol or propylene glycol. In contrast, ionic isotonising agents such as sodium chloride are generally unsuitable in the context of this invention. The novel solutions will contain the isotonising agent, if present, in an amount sufficient to bring about the formation of an approximately isotonic solution. The expression "an approximately isotonic solution" will be taken to mean in this context a solution that has an osmolarity of c. 300 milliosmol (mOsm), conveniently 300±10% mOsm. It must be borne in mind that all components of the solution contribute to the osmolarity. The non-ionic isotonising agent, if present, is added in customary amounts, i.e. preferably in amounts of about 3.5 percent by weight, preferably in amounts of about 1.5 to 3 percent by weight.

Substances that regulate the pH are suitably acids. It has been found that, surprisingly, the stability of the novel solutions is markedly high in the range of pH 4.5–5. It is, however, generally accepted that the tendency of e.g. fluorescein diacatete to hydrolysis is diminished in the acid range. It is therefore advantageous to add an acid in an amount suitable to adjust the pH of the novel solution to a value in the range from about 2.5 to about 6, preferably from about 4 to 5.5 and, most preferably, from 4.5 to 5. Suitable acids are typically organic mono- or dicarboxylic acids such as acetic acid, citric acid, tartaric acid, lactic acid or propionic acid, or inorganic acids such as hydrochloric acid, sulfuric acid or phosphoric acid.

A solvent in the final novel solution is not absolutely necessary, but is extremely useful in the preparation of the solutions. Thus it is advantageous to mix a solution of the fluorescein diester in a solvent with an aqueous solution of the β-cyclodextrin derivative. The solvent can be removed after fixing the aqueous β-cyclodextrin phase and the solvent phase containing the fluorescein diester, typically by evaporation under mild conditions or by lyophilisation. The solvent may, however, remain in the solution, preferably when the solution is an ophthalmologically acceptable solution. Suitable solvents are polar organic aprotic solvents, typically ethyl acetate, dimethyl sulfoxide, dimethyl formamide or acetone. Solvents, if present in the novel solutions, are added in amounts of up to 5 percent by weight, preferably in amounts of up to 1 percent by weight.

Solubilisers such as Cremophor types, preferably Cremophor RH 40, or Tween types or other customary solubilisers, may be added to the novel solutions in standard amounts.

Thickeners may also be added to the novel solutions in standard amounts, typically organic cellulose ethers such as hydroxypropyl methyl cellulose, or hyaluronic acid salts such as the sodium salt of hyaluronic acid. Customary buffers can also be added in standard amounts.

A further preferred embodiment of the invention therefore relates to a solution comprising a fluorescein di-lower alkyl ester and a partially etherified β-cyclodextrin the ether substituents of which are hydroxyethyl, hydroxypropyl or dihydroxypropyl groups, a non-ionic isotonising agent, an acid and an optional solvent.

A particularly preferred embodiment of the invention relates to a solution comprising a fluorescein di-lower alkyl ester and a partially etherified β-cyclodextrin the ether substituents of which are hydroxyethyl, hydroxypropyl or dihydroxypropyl groups, sorbitol as non-ionic isotonising agent, acetic acid as acid and ethyl acetate as optional solvent. Preferably the fluorescein di-lower alkyl ester is fluorescein diacetate and the partially etherified β-cyclodextrin is hydroxypropyl-β-cyclodextrin.

The invention relates very particularly to a solution comprising a) about 60 to about 100 micromol/l of fluorescein diacetate, b) about 5 to about 12 percent by weight of hydroxypropyl-β-cyclodextrin, c) sorbitol for adjusting the solution to an osmolarity of about 300 milliosmol, d) acetic acid for adjusting the pH range of the solution to about 4.5–5, and e) optionally ethyl acetate in an amount of up to about 5 percent by weight.

The invention also relates very particularly to a dry formulation comprising a) about 60 to c. 100 micromol/l of fluorescein diacetate, b) about 5 to about 12 percent by weight of hydroxypropyl-β-cyclodextrin, c) sorbitol for adjusting the solution to an osmolarity of about 300 milliosmol, the indicated amounts or concentrations being based in each case on the aqueous solution to be reconstituted.

The novel solutions are prepared in per se known manner by conventional mixing of the components. The procedure advantageously comprises the use of a solvent, preferably ethyl acetate, for dissolving the fluorescein diester. The β-cyclodextrin ether is dispersed in water. Both solutions are then mixed together. The remaining components may already be present in the aqueous solution of the β-cyclodextrin or are subsequently added to the combined solution of aqueous phase and solvent phase. If necessary, the solvent can be removed from the solution, conveniently by evaporation under mild conditions or by lyophilisation.

The novel solution is storable in the frozen state (unchanged after storage for 3 months). It is stable for at least 3 months in a refrigerator, i.e. at c. 8° C., and for 2 to 3 weeks at room temperature.

The preparation of the novel dry formulation can also be effected in per se known manner, conveniently from the novel solutions. Thus a solution can be evaporated to dryness under mild conditions, especially after the addition of solvents for azeotropic removal of water, typically a mixture of toluene and ethanol. The residue is thereafter conveniently dried, e.g. for some hours in a drying oven. The residue so obtained consists essentially of a hydroxypropyl-β-cyclodextrin-fluorescein diacetate complex as well as—if present in the solution—the isotonising agent, typically sorbitol.

The dry formulations of this invention are storable. Novel aqueous solutions can be reconstituted therefrom without the further addition of organic solvents.

In another of its aspects, the invention relates to the use of the novel solution in the photodynamic therapy of living cells, especially for the prevention of secondary cataract. Fluorescein diacetate has already been mentioned in connection with therapeutic methods. Thus EP-A-279 757 teaches, inter alia, the use of fluorescein diacetate for the selective destruction of transformed cells or tumour cells. This is done by microinjecting a substance like fluorescein diacetate into tumour cells. The tumour cells are killed by subsequent radiation. EP-A-279 757 contains no specific references to the nature and concentration of the solution of fluorescein diacetate to be used. Likewise there is no indication of a utility for the prevention of secondary cataract.

In contradistinction thereto, the use of the novel solutions makes a useful contribution to the prevention and treatment of secondary cataract that is not obvious from the known prior art. For the purposes of better understanding, this use will be hereinafter described in detail by means of the fluorescein diacetate which has been investigated most closely.

Fluorescein diacetate (FDA) is a non-fluorescing ester that is taken up by most living cells and hydrolysed. The fluorescing product, fluorescein, is generated from the cells again only slowly. Fluorescein therefore accumulates temporarily in the cells. The higher the extracellular concentration of FDA, the higher the resultant intracellular concentration of fluorescein. For example, in T4 tumour cells plateau concentrations of 25 μm of fluorescein are reached over 10 minutes by using a 1 μm FDA solution or of 70 μm of fluorescein if a 100 μm FDA solution is used. The fluorescein within a cell has a half-life of about 15 minutes. Irradiation of intracellular fluorescein with energy of suitable wavelength of about 480 nm causes a green light emission having a maximum of 515 nm. Intensive irradiation reduces the intensity of fluorescein. Living cells containing fluorescein die when the irradiation intensity is sufficiently high. The lower the intracellular concentration of fluorescein, the higher the critical irradiation energy needs to be. The intensity of the irradiation can therefore be chosen such that cells that contain only a minor amount of or no fluorescein are not impaired.

The above described method is thus based on the induction of local cytotoxicity by the selective and locally precisely defined irradiation of intracellular fluorescein at specific targets of organs. This is accomplished using a beam of light of controlled intensity and wavelength of light, preferably with a laser or a quartz iodine lamp, said beam of light being focussed precisely on the desired site. The irradiated cells containing fluorescein are thereby killed, whereas the sorrounding tissue is not damaged. Those skilled in the art will be familiar with the laser technology suitable and available for the purpose. The local photoactivation caused by a focussed laser beam that strikes intracellular fluorescein requires very much less local light energy than conventional laser technology based on cell burning.

Now the problem is that fluorescein is virtually not taken up by living cells. In contradistinction thereto, the ester FDA is readily taken up by most living cells and the esterase product, fluorescein, is released only slowly again into the extracellular fluid. Loading the intracellular space of cells with fluorescein is, however, complicated by the fact that FDA is also hydrolysed by esterases in the extracellular fluid. The amount of FDA available for cell loading is thereby reduced. For reproducible clinical use it is therefore advisable to lower the concentration of extracellular esterases. This is conveniently done by washing the environment of the particular area which it is desired to treat. A further problem may arise from the fact that the FDA diffuses away from the site of actual use and, as a consequence thereof, is also taken up by cells that are not to be treated at all. This problem can be countered by optimising the local application of FDA as well as the defined irradiation, typically by using a particularly well focussed beam of light.

The main procedure when using FDA in the above described photodynamic therapy, in which local phototoxicity is induced by FDA, can be exemplified as follows: a) The area to be treated is washed with physiological sodium chloride solution to remove extracellular body fluids at each site. b) The area to be treated is incubated for about 10 minutes with 40 μm of FDA in a solution of sodium chloride to load the cells with fluorescein. c) The incubated area is washed with a solution of sodium chloride to remove FDA that has not been taken up. d) The area is examined by irradiation with light of low energy so as to be able to distinguish the target cells without already inducing cytotoxicity. e) Over 10 to 30 minutes, selected target cells are irradiated for about 15 seconds to several minutes, e.g. for up to 3 minutes, with focussed light of high energy in order to induce cytotoxocity locally. f) Finally, the area is washed once more to remove residues and to facilitate the diffusion of fluorescein from the other cells.

By cataract is meant an opacity of the crystalline eye lens. Cataract can greatly impair vision to the point of blindness. Surgical removal of the lens and the insertion of an intraocular lens can restore vision. Extracapsular surgery of this so-called primary cataract is generally preferred, as fewer side-effects occur and also because of the ease with which artificial lenses can be inserted. The posterior capsule of the lens is left intact, whereas about one quarter of the anterior capsule of the lens is removed for extraction of the lens. In about 50% of all cases, the epithelium on the anterior side of the residual anterior lens membrane grows to the anterior part of the posterior membrane and thus causes secondary cataract. At the present time these membranes are normally removed by laser irradiation. In about 50% of cases, however, this type of treatment causes destruction of the posterior membrane, resulting in about 5% of cases in loss of sight of the eye operated on, typically owing to edema of the macula densa. Among such cases, up to 2.5% of patients are affected who were originally operated on for primary cataract. If the epithelial cell layer of the equatorial and anterior membrane of the capsule of the eye lens were removed, then secondary cataract could not occur.

Surprisingly, it is possible to use the formulations/solutions of this invention for solving this problem. The principle of using highly concentrated solutions of fluorescein diesters, as exemplified by FDA, can be described as follows.

Surgery on the eye is performed in accordance with the standard procedure until the lens has been extracted. The lens cavity is then washed with physiological sodium chloride solution and filled with novel FDA solution. The solution is allowed to act for about 10 minutes and washed once more to remove excess FDA. Using a non-focussed laser beam at c. 480 nm (e.g. an argon blue laser) and at low energy the lens epithelial cells are visualised by the intracellular green fluorescence. The anterior and posterior membrane of the lens are scanned for approximately the next 20 minutes and positions with cells are subsequently irradiated with the now well-focussed laser beam (depth of focus 1/10 to 1/100 mm) for about 10 to 20 seconds and with an energy that is greater than the energy that was previously used for visualisation. Finally, the cavity is washed once more and the operation is further performed in accordance with the standard procedure by inserting the artificial lens etc.

Alternatively, cells within the epithelium of the lens capsule can also be killed by injecting FDA solution subcapsularly direct into the still intact lens (hydrodissection in conjunction with FDA). Cell loading can be observed at low energy with an argon laser. Excess FDA is washed out together with nuclear fragments and thereafter irradiation of the target cells is carded out with high energy. Inexactly applied FDA can also be taken up by cells other than cells of the lens epithelium. This circumstance, however, only causes cytotoxicity if these cells are sufficiently loaded with fluorescein and are irradiated over a period of about 20 minutes. This can be avoided if irradiation is carried out for observation purposes at low energy and the actual high-energy irradiation is carded out only with a focussed beam of light at sites previously selected by scanning.

In a manner essentially analogous to that described above in connection with secondary cataract, the novel solutions can also be used for treating diseases by the basic principle of photodynamic therapy.

One example hereof is primary melanosis of the conjunctiva. In this case, the concentration of the extracellular esterases would first have to be reduced by conveniently washing the conjunctival sac with physiological sodium chloride solution. Novel FDA solution is then added to the conjunctival sac for an incubation time of about 10 minutes. Excess FDA is removed by intensive washing. Over the next 20 minutes the tumour is irradiated with a focussed laser beam under visual control, followed by further washing with physiological sodium chloride solution. This procedure can be repeated several times at any desired intervals so that cells can be removed layerwise. In order to avoid unwanted activation of intracellular fluorescein, all process steps from the time of FDA application up to 50 minutes before removal of FDA should be carried out in green-red light (>530 nm) as a precautionary measure.

The process for irradiating target cells that are loaded with novel solutions and which contain fluorescein caused by the action of esterase can be used for all target cells to be treated that are accessible for a local washing procedure from a surface, for a local incubation with a FDA solution and for local irradiation with a focussed laser beam. An essential prerequisite for carrying out the method is the presence of either a natural cavity or of a cavity artificially formed by a surgical operation. Such a surgical operation can conveniently be performed by inflating the proximal or distal end of the target area in a tubular tissue. Exemplary thereof are benign or malignant tumours of the oral or nasal cavity, also of the oesophagus or of the intestinal tract, or the urogenital tract, or of the cavities of joints. It should thus be possible to use the method in rectoscopy or in transurethral prostate surgery. Moreover, the method may be presumed to have utility for treating skin tumours if the incubation medium is administered with FDA locally either as viscous drops or in a bell jar that covers the tumour.

A basic aspect of photodynamic therapy using FDA is that the higher the local intracellular concentration of fluorescein, the less energy is required for irradiation. Furthermore, the precision of the irradiation is markedly enhanced when the local intracellular concentration of fluorescein is high. A selective destruction of cells can therefore only then be effected while surrounding tissue is simultaneously protected from damage. Hence to achieve the aim of a high local intracellular concentration of fluorescein it is of the utmost importance to provide highly concentrated solutions of FDA. This object is achieved in the practice of this invention for the first time, as it was not possible in conventional manner to bring the necessary amounts of fluorescein diester, conveniently FDA, into the form of stable formulations, preferably of aqueous solutions. Accordingly, it was heretofore also not possible to build up the requisite and desirably high concentrations of fluorescein intracellularly.

The invention is illustrated by the following Examples, but without being in any way restricted to the scope thereof.

EXAMPLE 1

200.00 g of Encapsin HPB (hydroxypropyl-β-cyclohextrin) and 57.0 g of sorbitol are added to and dissolved in 784.12 g of water (sterile water for injection). The pH is then adjusted to 4.5 with 1% acetic acid. Afterwards fluorescein diacetate, dissolved in ethyl acetate (2.88 g of a solution of 1250 mg of fluorescein diacetate in 100.0 ml of ethyl acetate), is added and the solution is mixed with the aqueous phase. The solution is subjected to sterile filtration. 40.00 g of Methocel E4M are dissolved in 960.00 g of water (sterile water for injection) and the solution is autoclaved. Both solutions are mixed in the ratio 1:1, giving a solution having a pH of 4.5±0.3 and a molarity of about 300 mOsmol/kg.

EXAMPLE 2

A solution comprising the following components is prepared in general accordance with the procedure described in Example 1:

| | |
|---|---|
| Encapsin HPB (hydroxypropyl-β-cyclodextrin) | 100.00 mg |
| sorbitol | 28.50 mg |
| acetic acid 1% | q.s. |
| fluorescein diacetate | 0.0333 mg |
| ethyl acetate | 2.88 mg |
| sterile water for injection to make up | 1 ml |

This solution contains 80 μmol/l of fluorescein diacetate. It is a clear, colourless solution having a pH of 4.72 and an osmolarity of 313 mOsmol/kg.

EXAMPLE 3

The solution of Example 2 has the following properties after storage for 1 month: after storage at −18° C. the pH is 4.61, the osmolarity is 306 mOsmol/kg, the concentration of fluorescein diacetate is still 99.8% of the initial concentration. After storage at +8° C. the pH is 4.57, the osmolarity is 304 mOsmol/kg, the concentration of fluorescein diacetate is still 94.0% of the initial concentration. After storage at +25° C. the pH is 4.51, osmolarity is 298 mOsmol/kg, and the concentration of fluorescein diacetate is still 69.7% of the initial concentration.

EXAMPLE 4

To 5.0 ml of the solution of Example 2 are added 40 ml of abs. ethanol and 10 ml of toluene (the 4:1 mixture of ethanol:toluene is used to remove water as an azeotrope). This mixture is concentrated to dryness on a rotary evaporator at a water bath temperature of 80° C. To remove solvent residues, the residue is dried for 22 hours at 120° C. in a drying oven. The resultant dry formulation virtually consists of hydroxypropyl-β-cyclohextrin-fluorescein diacetate complex as well as sorbitol as isotonic agent. It can be dissolved again at any time in water without the further addition of organic solvents.

The stability test (by HPLC) of an aqueous solution reconstituted from a dry formulation stored for 3 months exhibits no decrease of FDA or any other tendency to decomposition. This means that the novel dry formulation remains stable over a long period and is stable at room temperature (15°–25° C.). The reconstituted solution is intended for immediate use and is stable for at least 2 hours.

EXAMPLE 5

The intracellular uptake and generation of fluorescein (fluorescing) from FDA (non-fluorescing) is investigated in tissue culture using individual human T24 carcinoma cells by means of microscopic fluorimetry (excitation 480 nm; emission 520 nm). The intracellular fluorescein concentration rises linearly for about 4 minutes and reaches approximately plateau values after 10 minutes. It depends on the concentration of the added extracellular FDA: after 10 minutes the intracellular fluorescein concentration is 0.017 mmol/l with 0.04 mmol/l of FDA, 0.015 mmol/l with 0.02 mmol/l of FDA, 0.01 mmol/l with 0.01 mmol/l of FDA and 0.004 mmol/l with 0.001 mmol/l of FDA, whereas the fluorescein concentration with 0.0001 mmol/l of FDA is no longer measurable. No uptake can be observed if pure fluorescein is added to the cells. After removal of FDA from the tissue culture medium, the generation of fluorescein from the cells can be measured. The exclusion of fluorescein from the individual cells follows first order kinetics, and the half-life is about 10 to 25 minutes. The intensity of fluorescence of intracellular fluorescein fades when the fluorescein is correspondingly excited. The higher the intracellular concentration of fluorescein at a given irradiation energy, the stonger this fading is: the lower level for a fading effect is 0.004 mmol/l of intracellular fluorescein for 71 mJ/mm$^2$ and 0.002 mmol/l for 560 mJ/mm$^2$ (irradiation time 120 seconds). Irradiation for 1 to 10 minutes with 0.1 mW/mm$^2$ (for observation of the cells) effects no measurable fading.

EXAMPLE 6

The cytoxic action of irradiation (excitation 480 nm) of intracellular fluorescein from FDA is investigated using tissue culture of human T24 carcinoma cells. This is done by fluorometric determination of the intracellular fluorescein concentration under a microscope (excitation 480 nm; emission 520 nm) in single cells and the vitality via the uptake of propidium iodide. The lower the intracellular fluorescein concentration, the lower the cytotoxic effect. An intracellular fluorescein concentration of <0.0015 mmol/l of fluorescein and a fading of <0.001 mmol/l of fluorescein effect no cytotoxicity, not even under extreme irradiation conditions such as 1.2 J/mm$^2$ (for 2 minutes). At the same irradiation intensity, the higher the intracellular fluorescein concentration and the irradiation time are, the more marked the cytotoxic effect is. 50% of the cells are killed with 200 mJ/mm$^2$ if cells are irradiated with 0.013 mmol/l of intracellular fluorescein for 15 seconds, or if cells are irradiated with 0.005 mmol/l of fluorescein for 120 seconds, or killed with 500 mJ/mm$^2$ if cells are irradiated with 0.007 mmol of fluorescein for 15 seconds, or if cells are irradiated with 0.003 mmol of fluorescein for 120 seconds.

EXAMPLE 7

The intracellular uptake of fluorescein from FDA dissolved in the viscous medium Hymecel® (hydroxypropylmethyl cellulose) is investigated using tissue culture of human T24 carcinoma cells. This is done by fluorometric determination of the intracellular fluorescein concentration under the microscope (excitation 480 nm; emission 520 nm) in single cells. The increase in intracellular fluorescein concentration and plateau values approximately match those after incubation of the cells in aqueous medium. Eight minutes after removal of the viscous solution and washing the cells, the intracellular fluorescein concentration is 0.004 to 0.005 mmol/l after 0.01 mmol/l of FDA, 0.007 to 0.009 mmol/l after 0.02 mmol/l of FDA and 0.019 mmol/l after 0.04 mmol/l of FDA.

EXAMPLE 8

The cytotoxic effect of the irradiation of intracellular fluorescein with 488 nm laser light (argon) is investigated in vivo on rabbit eye cornea. FDA solution is dropped on to the cornea for 10 minutes, followed by washing with physiological sodium chloride solution. Irradiation is afterwards effected. The intensity of florescence on the cornea rises sharply during this time, then slowly falls to zero over about 5 hours after washing. Irradiation of the fluorescing cornea results in black specks the size of which matches the area irradiated by the laser. The lowest effective energy for this fading effect is about 2.4 J/mm$^2$ with 0.01 mmol/l of FDA and 0.11 J/mm$^2$ with 0.02 mmol/l of FDA. The macroscopically visible black specks correspond histologically to areas of dead epithelial cells in the outermost layer of the cornea. The lower limit of the irradiation energy for this cytotoxic effect is up to 0.38 mJ/mm$^2$ (5 seconds and 20 seconds) using 0.02 mmol/l of FDA.

EXAMPLE 9

The cytotoxic effect of the irradiation of intracellular fluorescein with 48 nm laser light (argon) is investigated in vivo on rabbit lens epithelium. This is done by first treating both rabbit eyes with Voltaren® eye drops (3 times over 24 hours) and expanding the pupillae with a mydriatic. The rabbits are operated on under a full anaesthetic. After a small incision of the cornea, the anterior chamber of the eye is thoroughly rinsed for 1 minute with sodium chloride solution (to remove natural chamber water), then slowly rinsed with 5 ml of FDA solution (1 ml/min) and filled, thereafter kept for a further 5 minutes and once more rinsed with sodium chloride solution for 1 minute (to remove excess FDA solution). While washing the chamber with FDA solution, sodium chloride solution is dropped onto the cornea (for rapid dilution and removal of the FDA solution flowing back from the chamber). Observation of the lens under a stereomicroscope in the epifluorescent mode shows a constant marked increase of fluorescence of the anterior lens capsule. In addition, the cornea surface in the closer environment of the incision site also fluoresces minimally. Finally, irradiation (0.92 W to 0.64 W) is carded out for 30 seconds, the circular irradiation surface on the plane of the lens being 95 mm$^2$ (11 mm diameter). After irradiation, the lens surface no longer fluoresces. The histological evaluation of the eyes (serial sections) of rabbits so treated and sacrificed about 18 hours later affords proof of the cytotoxic effect on the epithelium in the irradiation field: total necrosis of the lens epithelium and microscopically unchanged basal membrane, pyknotic nuclear residues and edematous swelling of the anterior subcapsular area of the lens. All investigated irradiation doses (291 mJ/mm$^2$ to 19 mJ/mm$^2$) were effective. In contradisctinction thereto, eyes that were irradiated but not injected with FDA solution exhibited no histopathologically detectable changes.

What is claimed is:

1. A formulation comprising:
   (a) a fluorescein diester; and
   (b) a partially etherified β-cyclodextrin, wherein the ether substituents of said β-cyclodextrin are selected from the group consisting of hydroxyethyl groups, hydroxypropyl groups, dihydroxypropyl groups, methyl groups, and ethyl groups.

2. A formulation according to claim 1, wherein the β-cyclodextrin ether has a water-solubility of more than 1.8 g in 100 ml of water.

3. A formulation according to claim 1 comprising a fluorescein di-lower alkyl ester and a partially etherified β-cyclodextrin the ether substituents of which are selected from the group consisting of hydroxyethyl, hydroxypropyl and dihydroxypropyl groups.

4. A formulation according to claim 1 comprising a fluorescein diacetate and a partially etherified β-cyclodextrin the ether substituents of which are hydroxyethyl, hydroxypropyl or dihydroxypropyl groups.

5. A formulation according to claim 1 comprising a fluorescein di-lower alkyl ester and a partially etherified β-cyclodextrin the ether substituents of which are hydroxypropyl groups.

6. A formulation according to claim 1 additionally comprising one or more components selected from the group consisting of isotonising agents, pH regulators, solvents, solubilisers, thickeners and buffers.

7. A formulation according to claim 6 comprising a fluorescein di-lower alkyl ester, a partially etherified β-cyclodextrin the ether substituents of which are hydroxyethyl, hydroxypropyl or dihydroxypropyl groups, sorbitol as non-ionic isotonising agent, acetic acid as acid and ethyl acetate as optional solvent.

8. A formulation according to claim 7, wherein the fluorescein di-lower alkyl ester is fluorescein diacetate and the partially etherified β-cyclodextrin is hydroxypropyl-β-cyclodextrin.

9. A formulation according to claim 2, 3, 4, 5, 6, 7, 8 or 1 which is an aqueous solution.

10. A solution according to claim 9 which contains the fluorescein diester in a concentration of up to about 200 micromol/l (200 μmol/l), preferably in a concentration of about 40 to about 200 micromol/l, more particularly in a concentration of up to about 100 micromol/l and, most preferably, in a concentration of about 60 to about 100 micromol/l.

11. A solution according to claim 9 comprising about 40 to about 200 micromol/l of fluorescein diacetate and about 1 to 20 percent by weight of hydroxypropyl-β-cyclodextrin.

12. A solution according to claim 9 which contains about 60 to about 100 micromol/l of fluorescein diacetate and about 5 to about 12 percent by weight of hydroxypropyl-β-cyclodextrin.

13. A solution according to claim 9 comprising
   a) about 60 to about 100 micromol/l of fluorescein diacetate,
   b) about 5 to about 12 percent by weight of hydroxypropyl-β-cyclodextrin,
   c) sorbitol for adjusting the solution to an osmolarity of about 300 milliosmol,
   d) acetic acid for adjusting the pH range of the solution to about 4.5–5, and
   e) optionally ethyl acetate in an amount of up to about 5 percent by weight.

14. A formulation according to claim 2, 3, 4, 5, 6, 7, 8 or 1 which is a dry formulation.

15. A formulation according to claim 14 comprising
   a) about 60 to c. 100 micromol/l of fluorescein diacetate,
   b) about 5 to about 12 percent by weight of hydroxypropyl-β-cyclodextrin,
   c) sorbitol for adjusting the solution to an osmolarity of about 300 milliosmol, the indicated amounts or concentrations being based in each case on the aqueous solution to be reconstituted.

16. A method of loading living cells with fluorescein, comprising contacting living cells with an incubation medium which is an aqueous formulation comprising a fluorescein diester and a partially etherified β-cyclodextrin, the ether substituents of which are selected from the group consisting of hydroxyethyl groups, hydroxypropyl groups, dihydroxypropyl groups, methyl groups, and ethyl groups.

17. A method of claim 16 further comprising the step of utilizing said living cells in photodynamic therapy.

18. A method of claim 17 wherein said photodynamic therapy is applied for the prevention of secondary cataract.

19. A formulation according to claim 6, comprising:
   (a) a fluorescein di-lower alkyl ester;
   (b) a partially etherified β-cyclodextrin, the ether substituents of which are selected from the group consisting of hydroxyethyl, hydroxypropyl and dihydroxypropyl groups;
   (c) a non-ionic isotonizing agent; and
   (d) an acid.

20. A process for the preparation of a solution including about 60 to about 100 micromol/L fluorescein diacetate about 5 to about 12 weight percent hydroxypropyl-β-cyclodextrin, sorbitol, a solvent and water, said preparation process comprising the steps of:
   (a) dispersing hydroxypropyl-β-cyclodextrin in water to form a dispersion;
   (b) dissolving fluorescein diacetate in a solvent to form a solution;
   (c) mixing said dispersion with said solution; and
   (d) adding sorbitol to adjust tonicity.

21. A process of claim 20 wherein said tonicity is adjusted to about 300 milliosmols.

* * * * *